United States Patent [19]

Roses et al.

[11] Patent Number: 5,767,337

[45] Date of Patent: Jun. 16, 1998

[54] CREATION OF HUMAN APOLIPOPROTEIN E ISOFORM SPECIFIC TRANSGENIC MICE IN APOLIPOPROTEIN DEFICIENT "KNOCKOUT" MICE

[75] Inventors: Allen D. Roses; John R. Gilbert; Pu-Ting Xu; Donald E. Schmechel, all of Durham, N.C.

[73] Assignee: Duke University, Durham, N.C.

[21] Appl. No.: 509,521

[22] Filed: Jul. 31, 1995

[51] Int. Cl.$^6$ .............................. C12N 5/00; C12N 15/00; C12N 15/09; C12N 15/63

[52] U.S. Cl. ........................ 800/2; 435/172.3; 435/69.1; 435/320.1; 424/9.21

[58] Field of Search .......................... 800/2; 435/172.3, 435/69.1, 320.1; 424/9.21

[56] References Cited

U.S. PATENT DOCUMENTS 5,569,824  10/1996  Donehower et al. ................. 800/2
5,569,827  10/1996  Kessovs-Elbaz et al. ............ 800/2

FOREIGN PATENT DOCUMENTS

WO 90/06992  6/1990  WIPO .
WO 93/19166  9/1993  WIPO .
WO 94/09155  4/1994  WIPO .
WO 95/03397  2/1995  WIPO .
WO 95/03402  2/1995  WIPO .
WO 95/06456  3/1995  WIPO .
WO 95/16791  6/1995  WIPO .
WO 95/29257  11/1995  WIPO .

OTHER PUBLICATIONS

D. Games et al.; *Alzheimer–type neuropathology in transgenic mice overexpressing V717F β–amyloid precursor protein*, Letters 373:523–527 (1995).

Bowman et al., *"Discovery of a Brain Promoter from the Human Transferrin Gene and Its Utilization for Development of Transgenic Mice That Express Human Apolipoprotein E Alleles"*, Proc. Natl. Acad. Sci. USA, vol. 92, Dec. 1995, pp. 12115–12119.

Xu et al., *"Expression of Human Isoform Specific Apolipoprotein E2 and E4 in Transgenic Mice"*, American Journal of Human Genetics, vol. 57, No. 4 sup, Oct. 1995, p. 254.

Bellosta et al., *"Macrophage–specific Expression of Human Apolipoprotein E Reduces Atherosclerosis in Hypercholesterolemic Apolipoprotein E–null Mice"*, J. Clin. Invest., vol. 96, Nov. 1995, pp. 2170–2179.

Smith et al., *"Accumulation of Human Apolipoprotein E in the Plasma of Transgenic Mice"*, The Journal of Biological Chemistry, vol. 265, No. 25, Sep. 5, 1990, pp. 14709–14712.

Simonet et al., *"Multiple Tissue–specific Elements Control the Apolipoprotein E/C–I Gene Locus in Transgenic Mice"*, The Journal of Biological Chemistry, vol. 266, No. 14, May 15 1991, pp. 8651–8654.

Simonet et al.; *"In the Absence of a Downstream Element, the Apolipoprotein E Gene Is Expressed at High Levels in Kidneys of Transgenic Mice"*; J. of Biol. Chem., 265(19):10809–10812 (1990).

Simonet et al.; *"A Far–downstream Hepatocyte–specific Control Region Directs Expression of the Linked Human Apolipoprotein E and C–I Genes in Transgenic Mice"*; J. of Biol. Chem., 268(11):8221–8229 (1993).

Fazio et al.; *"Type III Hyperlipoproteinemic Phenotype in Transgenic Mice Expressing Dysfunctional Apolipoprotein E"*; J. Clin. Invest., 92:1497–1504 (1993).

Wall Theriogenology 45:57–68 1996.

Bradley et al. Bio/Technology 10:534–538 1992.

Fazio et al. Artesiosclerosis and Thrombosis 14(11):1873–1879 (1994).

Plump et al. Cell 71:343–353 (1992).

Yeung et al J. Exp Med 180:1911–1920 (1994).

Primary Examiner—Jasemine C. Chambers
Assistant Examiner—Jill D. Schmuck
Attorney, Agent, or Firm—Myers Bigel Sibley & Sajovec

[57] ABSTRACT

A transgenic mouse that expresses the human Apo E isoforms Apo E2, Apo E3 or Apo E4 but is essentially incapable of expressing endogenous Apo E. Additionally, mice that express more than one of these isoforms are produced by selectively breeding the transgenic mice expressing the different Apo E isoforms disclosed herein. Thus, the present invention allows, among other things, the study of the effects of different combinations of human Apo E isoform expression on normal brain biology, development, function, aging and injury.

6 Claims, 1 Drawing Sheet

SCHEMATICS OF Apo E ISOFORM SPECIFIC COSMID CLONES SELECTED TO ISOLATE THE Apo E GENOMIC DNA FOR MICROINJECTION. k, Kpn I; c, Cla I; s, Sca I. Apo E3 CLONES, COS-3 AND COS-17; Apo E4 CLONES, COS-23 AND COS-28; AND Apo E2 CLONE, COS-45.

CREATION OF HUMAN APOLIPOPROTEIN E ISOFORM SPECIFIC TRANSGENIC MICE IN APOLIPOPROTEIN DEFICIENT "KNOCKOUT" MICE

This invention was made with Government support under NIH award AG-07922. The Government has certain rights in this invention.

FIELD OF THE INVENTION

The present invention concerns transgenic nonhuman animals containing human DNA coding for human apolipoprotein E isoforms Apo E4, Apo E3 or Apo E2 and which express these human proteins in vivo, and a method for screening a compound for the ability to effect Apo E activity in these animals

BACKGROUND OF THE INVENTION

Transgenic animals are characterized by the presence of exogenous DNA integrated in their genetic information. These animals express the genetic characteristic encoded by the foreign DNA. While the mechanism of integration of exogenous DNA has not been completely elucidated, several methods for the production of transgenic animals exist and include microinjection of exogenous DNA directly into embryos or introduction of foreign DNA into cells by the technique of calcium phosphate precipitation. For a review of the literature in this area, see PCT Application No. WO90/06992 of Lo et al.

Human apolipoprotein E (Apo E) is a lipid transport protein that exists in three common isoforms: Apo E2, Apo E3 and Apo E4. The absence of a functional Apo E gene in mice is associated with hypercholesterolemia. (See J. Piedrahita et al., *Proc. Natl. Acad. Sci.* 89, 4471 (1992)). Apo E is also associated with Alzheimer's Disease; the possession of an Apo E4 allele has been shown to be a risk factor for the development of Alzheimer's Disease while possession of an allele of the isoform Apo E2 has been shown to have a protective or delaying effect on the onset of this disease. (See PCT Application No. 5405-75B-1 of Roses et al.). These isoforms exist at a frequency of about 8%, 76% and 16% respectively, in the population of the United States. (See, e.g., J. Poirier et al., *Lancet* 342, 697 (1993)).

SUMMARY OF THE INVENTION

The present invention is a transgenic nonhuman animal that expresses the human Apo E isoforms Apo E2, Apo E3 or Apo E4. The animals are essentially incapable of expressing the endogenous Apo E. Additionally, animals that express more than one of these isoforms can be produced by selectively breeding the transgenic animals expressing the different Apo E isoforms disclosed herein. Thus, the present invention allows, among other things, the study of the effects of different combinations of human Apo E isoform expression on normal brain biology, development, function, aging and injury.

A second aspect of the present invention is a method of screening a compound for the ability to effect the activity of Apo E isoforms in transgenic animals comprising treating transgenic animals with the compound, assaying for effects of the compound on animal physiology and evaluating it for possible therapeutic potential.

A third aspect of the present invention is a transgenic animal, created by breeding different isoform specific transgenic animals to each other, that will allow the study and characterization of the biological effects of the different combinations of Apo E isoforms that are found in the human population.

The foregoing and other objects and aspects of the present invention are explained in detail in the drawings herein and the specification set forth below.

DETAILED DESCRIPTION OF THE INVENTION

Figure 1:
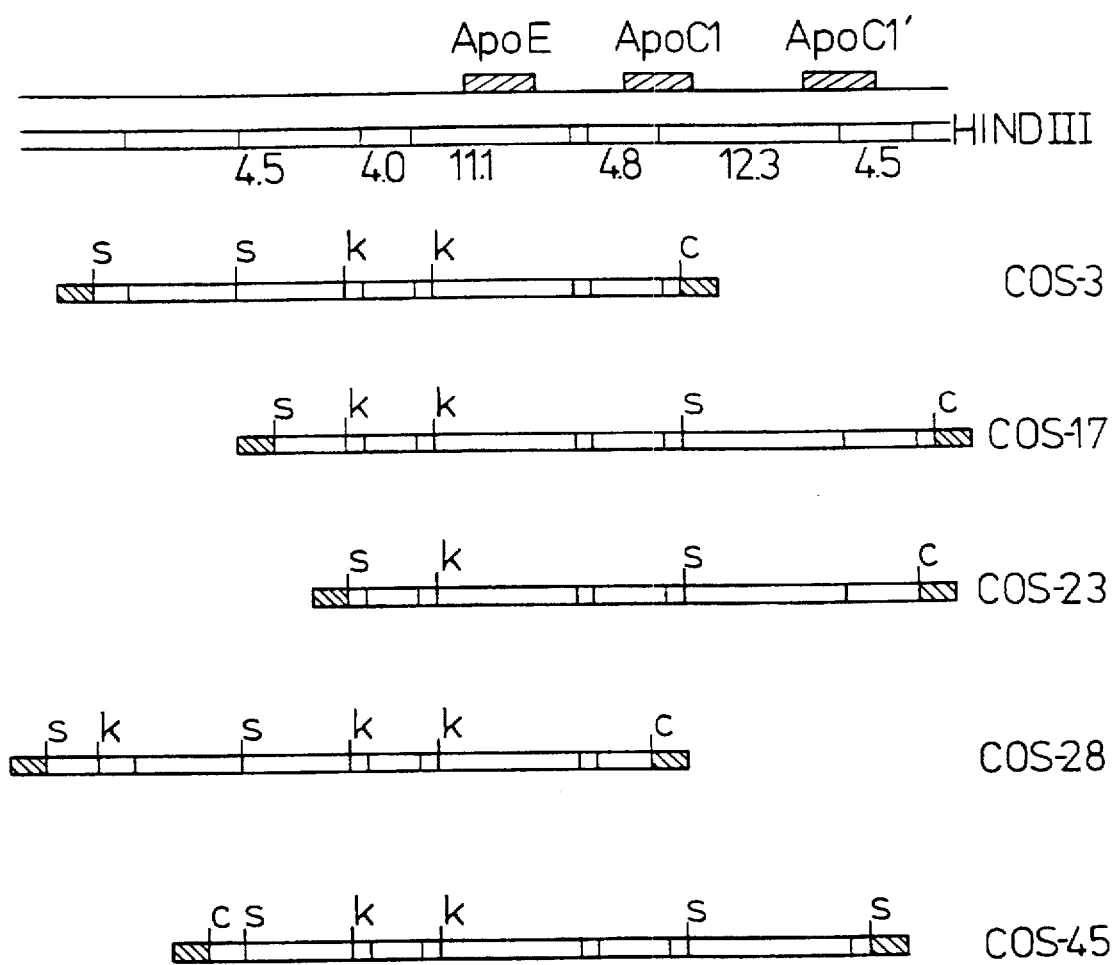
FIG. 1 illustrates Apo E specific cosmid clones selected to isolate the Apo E genomic DNA for microinjection. The letters k, c and s are abbreviations for the restriction enzymes Kpn I, Cla I and Sca I, respectively. Apo E3 clones are labeled COS-3 and COS-17; Apo E4 clones are labeled COS-23 and COS-28; and the Apo E2 clone is labeled COS-45.

Nucleotide sequences are presented herein by single strand only, in the 5' to 3' direction, from left to right.

Animals suitable for carrying out the present invention are, in general, nonhuman mammals, such as monkeys, dogs, cats, rats, and mice. Rodent species such as rat and mouse are preferred, and the mouse is the most preferred species. Animals in every stage of development, including juvenile, adolescent, and adult, are included in this description. The progeny of interbreeding the transgenic animals described in the present invention refers to transgenic animals expressing human Apo E isoforms in any and all various combinations, whether heterozygous or homozygous for a particular isoform (e.g., Apo E2/Apo E2; Apo E3/Apo E3; Apo E4/Apo E4; Apo E2/Apo E3; Apo E2/Apo E4; Apo E3/Apo E4).

Apo E "knockout" animals utilized in the present invention refers to mice whose endogenous Apo E gene has been disrupted by homologous recombination and which produce no functional Apo E of their own. ApoE knockout mice are known and have been bred by Dr. N. Maeda of the University of North Carolina at Chapel Hill in order to study the role of Apo E in lipid disorders.(See, e.g., Piedrahita et al., *Proc. Natl. Acad. Sci.* 83, 4471 (1992)). Apo E knockout animals of species other than mice can be produced by variation of the procedures carried to produce Apo E knockout mice that will be apparent to those skilled in the art.

ApoE knockout animals can be modified to contain and express DNA encoding a human DNA for an Apo E isoform by any suitable technique. The DNA encoding the human ApoE isoform is under the control of any suitable regulatory element for expressing the DNA, but is preferably operably associated with a mammalian ApoE promoter, and is most preferably operably associated with the human ApoE promoter. In one embodiment, the human DNA for Apo E isoforms employed to carry out the present invention is a 30,000 base pair (bp) sequence extending approximately 5,000 bp proximal (5') to the Apo E gene and to the Apo C1' pseudogene, which is approximately 15,000 bp distal (3') to the Apo E gene. The sequence contains all gene regulatory elements necessary for the normal transcription of the gene in mouse brain. (See, e.g., W. Simonet, *J. Biol. Chem.* 268, 8221 (1993)). In one embodiment of the instent invention, the gene utilized is was isolated from lymphoblasts of humans homozygous for the Apo E4, Apo E3 or Apo E2 allele.

Supercos1 and pWE 15 cosmid vectors (commercially available from Stratagene) may be used to carry out the present invention.

Human DNA for the Apo E isoforms cloned into the Supercos1 vector may be used to create Apo E isoform specific cosmid libraries which are screened with Apo E cDNA for cosmids expressing the human Apo E isoforms. Apo E genomic DNA is then isolated from selected cosmid clones and purified for microinjection into the pronucleus of mouse oocytes fertilized by "knockout" mice. The resulting mouse pups are referred to as founders (F0).

Colonies of transgenic mice are subsequently established by breeding F0 mice to "knockout" mice. Progeny of this mating (F1) contain the human Apo E gene but no functional mouse Apo E gene. F1 mice are then bred to "knockout" mice to create mice heterozygous for the human Apo E gene and which lack the functional mouse Apo E gene.

Once colonies of transgenic mice are established, several mice are sacrificed and analyzed for human Apo E gene integration efficiency and transcript expression. Those transgenic founder lines expressing a functional human Apo E gene are expanded and the progeny of the expansion used to study the effects of the human Apo E gene on animal physiology. Animals of the present invention preferably express the human ApoE at least in brain tissue and/or blood serum, and also express the human ApoE in heart, kidney, spleen, muscle, intestine, and liver tissue cells.

Animals of the present invention may be used as a source of human ApoE3, ApoE3, or ApoE4, which can be collected from the serum of the animal in accordance with standard techniques. Human ApoE3, ApoE3, or ApoE4, can in turn be administered to animal subjects as immunogens to raise anti-human ApoE antibodies therein, which antibodies are useful in human ApoE diagnostic assays.

In addition, the animals may be used to characterize the role of Apo E isoform specific differences in brain development, biology, function, aging and injury. The animals may be used for the study of the role of Apo E isoforms in the regulation of lipid metabolism. The role of Apo E and the importance of the various isoforms in the etiology of neural diseases such as Alzheimer's Disease may be determined by using animals of the present invention. Interbreeding transgenic mice expressing different Apo E isoforms may also generate a transgenic mouse model exhibiting full-blown Alzheimer's Disease symptomalogy which would be extremely useful for the study of the pathology of this disease.

Also disclosed herein is a method to study the effects of therapeutic intervention on the activity of Apo E isoforms in transgenic mice expressing these isoforms. Such a method comprises treating the transgenic animal with a compound and assaying or detecting the effect of the compound on animal physiology (e.g., progression of dementia, progression of amyloid plaque formation, etc.).

The animals are useful as a model that allows in vivo studies of the molecular and cellular biochemistry of Apo E isoforms and of interactions between Apo E isoforms and other proteins of interest. The animals are useful as a model that will allow the identification of potential activities of Apo E isoforms in nonneural tissue in animals in vivo. The animals are useful for studying the biological effects of the different combinations of Apo E isoforms that are found in the human population by breeding different isoform specific transgenic mice to each other and characterizing the biological effects of the resulting isoform combinations in the progeny.

Those skilled in the art will appreciate numerous variations which may be made to the foregoing in carrying out the instant invention, which will be readily apparent from the literature concerning transgenic animals. See, e.g., H. Chen et al., PCT Application WO 95/03397; H. Chen et al., PCT Application WO 95/03402; C. Wood et al., PCT Application WO 91/00906; C. Lo et al., PCT Application WO 90/06992; P. Leder et al., U.S. Pat. No. 4,736,866; and T. Wagner et al., U.S. patent application Ser. No. 4,873,191.

The present invention is explained in greater detail by the following Examples. These examples are illustrative of the present invention, and are not to be construed as limiting thereof.

EXAMPLE 1

Construction of Apo E Isoform Specific Cosmid Libraries

Isolation of high-molecular weight genomic DNA:

Human genomic DNAs used for construction of cosmid libraries were isolated and purified from lymphoblasts of individuals who were verified homozygous carriers for Apo E 2/2, 3/3 and 4/4 alleles. Lymphoblasts were propagated in DMEM (GIBCO-BRL) supplemented with 10% fetal calf serum (FCS) using standard procedures known in the art. $5 \times 10^7$ cultured lymphoblasts were harvested and washed once with cold phosphate-buffered saline (PBS) and resuspended in 15 ml of 20 mM Tris.HCl, pH 8.0, 10 mM NaCl, 1 mM ethylenediaminetetraacetic acid (EDTA), and digested with 100 mg/ml of proteinase K (Boehringer Mannheim, BMB) including 0.5% sodium dodecyl sulfate (SDS) at 50° C. for 6 hours or overnight. The DNA were extracted by gentle inversion with an equal volume of Tris.HCl (pH 8.0) saturated phenol/chloroform for 10 minutes at room temperature. The mixture was separated by centrifugation at 5000 rpm for 15 minutes at room temperature. The viscous aqueous phase was carefully collected and extracted once with an equal volume of chloroform. The clear aqueous phase was dialyzed at 4° C. four times against 4 liters of a solution of 50 mM Tris.HCl (pH 8.0), 10 mM EDTA. The concentration of the purified DNA was calculated by measuring the absorbance at wavelength of 260 and 280 nm and employing a mathematical formula known to those skilled in the art.

Preparation of 35–50 kilobase (kb) genomic DNA fragments:

In order to clone the genomic DNA fragment into a Bam HI site of the Supercos1 vector (Stratagene), the 150–200 kb high-molecular weight genomic DNA was partially digested with restriction endonuclease Mbo I (GIBCO-BRL) to produce 35–50 kb fragments. The optical time interval and quantity of Mbo I enzyme used for digestion were determined by a series test of partial digests. A sample digest of 10 ug of genomic DNA in a 100 ul reaction was cut by adding one unit of Mbo I enzyme. 15 ul aliquots were removed from the digestion at 0, 5, 10, 15, 20, 25 and 30 minute time points. 3 ul of 6× DNA gel loading buffer (0.25% bromophenol blue, 0.25% xylene cyanol FF and 30% glycerol prepared in water) was added immediately to stop reaction and the digested DNA were checked by electrophoresis on a 0.5% agarose gel. 100 ug of the genomic DNA was partially digested with Mbo I in a total volume of 1.0 ml at the conditions best mimicking the test digestion. After digestion, 18 ul of 0.5 mM EDTA (pH 8.0) was added to stop the reaction. The sample was extracted once with an equal volume of phenol/chloroform. The upper aqueous phase was adjusted to 0.3M NaOAc, pH 5.2 and precipitated with 2 volumes of ethanol. After centrifugation, the pellet was washed once with 70% ethanol, lyophilized and resuspended in water. The Mbo I-digested DNA was then dephosphorylated with 5 units of calf intestinal alkaline phosphatase (CIAP) (BMB) at 37° C. for 60 minutes. The reaction was stopped by adding 3 ul of 0.5M EDTA and incubated at 56° C. for 15 minutes. The sample was extracted once with phenol/chloroform and the aqueous phase was adjusted to 0.3M NaOAc and precipitated with 2 volumes of ethanol. The dried pellet was resuspended in water at a concentration of 1 mg/ml.

Preparation of Supercos 1 vector:

10 ug of Supercos1 vector DNA was digested with 50 units of XbaI enzyme (GIBCO-BRL) in a total volume of 200 ml in the standard buffer for 2 hours at 37° C. The digested vector DNA was extracted once with phenol/chloroform, precipitated with ethanol, lyophilized and resuspended in 50 ml of water. The XbaI-digested DNA was dephosphorylated with 5 units of CIAP and purified as described above. The Xba I/CIAP-treated vector DNA was then digested with 50 units of Bam HI enzyme in a total volume of 200 ul for 2 hours at 37° C. The DNA was purified by phenol/chloroform and precipitated with ethanol as described above.

Ligation and Packaging of DNA:

2.5 ug of the Mbo I digested genomic DNA was ligated with 1 ug of Xba I/CIAP/Bam HI-treated Supercos1 vector DNA using 2 units of T4 DNA ligase (BMB) in a total volume of 20 ul at 16° C. for 24 hours. The ligated DNA was packaged into cosmids using high efficient Gigapack II Packaging extract (Stratagene). 4 ml of the ligated DNA was added to each quickly thawed Freeze/Thaw extract, placed on ice and 15 ml Sonic extract was quickly added to the extract. After incubation at room temperature for 2 hours, 500 ml of SM buffer (100 mM NaCl, 10 mM MgSO4, 50 mM Tris.HCl, pH 7.5 and 0.01% gelatin) and 20 ml of chloroform were added to each packaging reaction. The solution was mixed gently and spun briefly to sediment debris and the supernatant was ready to be titered and screened.

EXAMPLE 2

Isolation of Isoform Specific Apo E Genomic DNA

Screening of cosmid libraries:

To isolate the isoform specific Apo E gene, the Apo E2, E3 and E4 isoform specific cosmid libraries were initially screened with Apo E cDNA and the positive clones were rescreened with an Apo C1 cDNA, this gene being located about 5.3 kb downstream of the Apo E gene. The DH5a-MCR (GIBCO-BRL) cell line was used as host cells. All the packaged cosmid libraries were screened according to Stratagene protocols. One to two million packaged recombinants from each of the cosmid libraries were spread on 137 mm Colony/PlaqueScreen discs (DU PONT). Each disc contained 40–50,000 cosmid clones. The discs were incubated on 150 mm LB/kanamycin plates (1.0% Bacto-tryptone, 0.5% Bacto-yeast extract, 150 mM NaCl, 1.5% Difco-agar and 50 mg/ml kanamycin) overnight at 37° C. Two replica filters were then made from the master filters and incubated overnight on LB/kanamycin plates at 37° C. The duplicated filters were denatured twice with 0.5N NaOH solution and neutralized twice with 1M Tris.HCl pH 7.5 for 5 minutes each at room temperature. The filters were blotted dry on paper towels and baked in a vacuum oven for 2 hours at 80° C. Prehybridization was carried out in 2× SSC (150 mM NaCl, 15 mM Sodium Citrate), 1.0% SDS, 10% dextran sulphate and 50% deionized formamide for one hour to overnight. Following prehybridization, $5\times10^6$ cpm of the Apo E cDNA probe prepared using Multiprimer DNA labelling system (Amersham) were added to the prehybridization solution and incubated overnight at 42° C. The filters were then washed in 0.1× SSC, 0.1% SDS at 55°–60° C. with 3 or 4 changes over 2–4 hours, blotted on paper towel and exposed to X-ray film overnight. Autoradiograms were aligned to master filters. A 1–5 mm region surrounding the hybridization signal was scraped with a sterile toothpick and put in 100 ml of LB medium containing 50 mg ampicillin. The bacteria were diluted and replated on 137 mm filters on 150 mm LB/kanamycin plates to give 500–1000 clones per plate. The replica filters were rehybridized with $^{32}$P-labeled Apo C1 probe. Single positive clones were isolated and inoculated in 3.0 ml culture.

Preparation of cosmid DNA from mini-lysates:

The bacterial cells were collected from 1.5 ml culture by centrifugation for 2 minutes in a microcentrifuge. The pellet was resuspended in 300 ul of STET (8% Sucrose, 0.5% Triton X-100, 50 mM Tris.HCl pH 8.0, 50 mM EDTA). 20 ul of fresh lysozyme (10 mg/ml) was added to the suspension and incubated in a boiling water bath for 1 minute, then centrifuged for 10 minutes at 4° C. The gelatinous pellet was removed and discarded. The remaining supernatant was precipitated with 300 ml of isopropanol. The pellet was washed with 70% ethanol, lyophilized and resuspended in 50 ml of water.

EXAMPLE 3

Generation of Transgenic Mice

Mice used for microinjection:

An Apo E "knockout" mouse line provided by Dr. N. Maeda of The University of North Carolina at Chapel Hill was used to generate human Apo E transgenic mice. The "knockout" mice carry an inactivated endogenous Apo E gene created by gene targeting in the embryonic stem cells. (See Piedrahita et al., Proc. Natl. Acad. Sci. 83, 4471 (1992)). Briefly, the normal mouse Apo E gene was disrupted by removing an Xho I/Bam HI fragment containing part of exon 3 and part of intron 3 and replacing it by the neomycin resistance gene. After homologous recombination between the endogenous Apo E locus and the targeting plasmid, the size of the Hind III-digested genomic DNA fragment hybridized to the Apo E probe increased from 6.5 to 7.5 kb. Thus, Southern blotting of Hind III-digested DNA from the targeting mice showed 6.5 and/or 7.5 kb bands indicating inheritance of normal and the modified allele, respectively, when probed with a mouse Apo E exon 4 DNA fragment amplified from mouse genomic DNA.

Purification of Apo E genomic DNA fragment for microinjection:

28–30 kb Apo E genomic DNA fragments were purified from the selected cosmid clones by digestion with the appropriate restriction enzyme(s) (KpnI, ClaI, ScaI, as will follow from the foregoing). 20 ug of cosmid DNA was digested with 50–100 units of selected enzymes in a total volume of 300 ul for 2 hours at 37° C. The digested DNA was mixed with 6× DNA loading buffer and separated on 0.7% agarose gel. The specific DNA band was cut from the gel, excess agarose trimmed away and the DNA was electroeluted into a dialysis bag at 300 V for 30 min. The DNA was washed and collected from the dialysis bag and purified by extracting with an equal volume of phenol, phenol/chloroform and chloroform respectively, and then precipitated and resuspended in 50 ul of injection buffer (10 mM Tris.HCl, pH 7.5, 0.1 mM EDTA).

Microinjection of Apo E genomic DNA:

The generation of transgenic animals through the microinjection of single-celled embryos involved four well-recognized steps: the isolation of fertilized eggs from pregnant animals; the injection of the transgene into the pronuclei of the single-celled fertilized embryos; the implantation of the injected embryos into the oviduct of a pseudopregnant female; and lastly, the analysis of the animals generated.

The female mice that acted as egg donors were hormonally stimulated to produce a greater yield of embryos by injection intraperitoneally with 5 international units (IU) of pregnant mare's serum (PMS) which stimulated follicular growth. This injection was followed 48 hours later by a second intraperitoneal injection of 5 IU of human chorionic gonadotropin (hCG) which potentiated the resumption of oocyte meiosis and ovulation. Even in strains that do not respond well to hormonal stimulation, a higher percentage of hormonally stimulated females plug than females in natural matings. Additionally, although hormonally stimulated matings result in a larger number of abnormal eggs than normal matings, this is more than compensated for by the greatly increased number of injectable eggs produced per female (an average of 15–40 for stimulated donors versus 8–12 for unstimulated donors).

Mice were maintained on a daily cycle of 12 hours of light followed by 12 hours of darkness. The dark period was maintained between 4 p.m. and 4 a.m., thus, fertilization occurred around midnight and the embryos were isolated the next morning. The oviduct was dissected away and placed in M2 culture medium in accordance with known techniques. Eggs were recovered using a dissecting microscope at 10×20× magnification and pipetted into a solution of 0.1% hyaluronidase to remove cumulus cells. Eggs were then washed in M2 medium and placed in droplets of M16 medium under paraffin oil in accordance with known techniques and incubated at 37° C. in 5% $CO_2$ until injection.

The DNA used must be extensively purified prior to microinjection to remove impurities that might be harmful to the eggs or clog the injection needles. DNA used for these experiments was prepared in two ways. The first involved restriction digestion with Kpn I and Cla I followed by separation of the fragments on agarose gels. Apo E containing transgenes were isolated by electro-elution, dialyzed, extensively extracted with butanol and precipitated. The second procedure involved using the elutrap system (Schleicher & Schuell, S&S) for DNA fragment isolation.

Microinjection utilized an inverted Olympus microscope with Nomarski differential interference contrast optics. The injection into the pronuclei was carried out using 1 picoliter of DNA solution and micromanipulators at 200× magnification on a vibration-free table. After injection, the eggs were returned to M16 medium under oil and incubated at 37° C. in 5% $CO_2$ overnight. Embryos that had divided into the two-cell stage by the next day were transferred to the oviduct of a pseudo-pregnant female. Although eggs may be transferred immediately to the oviduct, allowing the embryos to incubate overnight insured that only viable two-celled embryos were transferred.

Embryos that survived injection were transferred to the ampulla of the oviduct of a pseudo-pregnant female through the infundibulum. Pseudo-pregnant females were generated by mating vasectomized males to the females the night before transfers were to take place. About 15–20 eggs were transferred to one oviduct per female. The eggs also migrated into the opposite uterine horn and thus were implanted on both sides.

EXAMPLE 4

Characterization and Analysis of Transgenes

Screen of the transgenic mice by polymerase chain reaction:

Polymerase chain reaction (PCR) was performed to detect the presence of the human Apo E gene in the transgenic mouse pups and to identify their genotypes. Human Apo E exon 3 specific primers were derived from intronic sequences flanking exon 3 of the human Apo gene. The sequence of the forward primer used was 5'-GGTAGCTAGATGCCTGGACGG-3' (SEQ ID NO:1) and the reverse primer used was 5'-GCTAGAACCAGCAG AGACCC-3' (SEQ ID NO:2). Mouse knockout primers were synthesized from the mouse DNA sequence spanning the disrupted (knockout) region. The forward sequence of the knockout primer used was 5'-GTCTCGGCTCTGAACT ACTATG-3' (SEQ ID NO:3) and the reverse primer used was 5'-GCAAGAGGTGATGGTACTCG-3' (SEQ ID NO:4). Each PCR reaction contained 250–500 ng of mouse tail DNA, 100 ng of each primer, 200 mM each dNTP, 0.5 units of Taq DNA polymerase (GIBCO-BRL), in a final volume of 50 ul. An initial denaturation at 94° C. for 5 minutes was followed by 35 cycles of annealing at 65° C. for 0.5 minutes, extension at 70° C. for 1.5 minutes, denaturation at 94° C. for 0.5 minutes, and a final extension at 70° C. for 10 minutes.

Southern blot analysis:

The presence, the mode of integration and the copy numbers of transgenes in the transgenic mice were further confirmed by Southern blot analysis. 20 ug of mouse genomic DNA and 16 ug of human genomic DNA were digested with 100 units of appropriate enzyme in a total volume of 300 ul solution at 37° C. overnight. The digested DNA was precipitated with 2 volumes of ethanol and the pellet was washed with 70% ethanol, lyophilized and redigested with 20 units of the enzyme in a total volume of 30 ul at 37° C. for 2 hours. The DNA was separated on 0.7% agarose gel and blotted onto GeneScreen membrane (DU PONT) using Posiblot30—30 (Stratagene) following the manufacturer's protocol.

Results:

Results from PCR and Southern blotting analyses indicated that five transgenic founder animals were generated comprising the human Apo E4 gene. Three founder animals were generated concerning the human Apo E3 gene, and five were generated concerning the human Apo E3 gene. Southern blotting and human specific transgene PCR analysis of transgenic mouse genomic DNA that had been cut with the Hind III restriction enzyme and probed with human Apo E and Apo C1 cDNA, showed the presence of the human 11.1 kb Hind III band associated with the presence of cosmid 28 (Apo E4) and cosmid 45 (Apo E2) in the Apo E4 and Apo E2 transgenic animals, respectively. (Data not shown). Data also indicated that, while a founder line labeled E2-267 had the 11.1 kb Hind III fragment (indicating that the Sca I-Sca I fragment from Cos-45 had integrated), an Apo E2 founder line labeled E2-222 lacked the 11.1 kb fragment but possessed a larger hybridizing fragment. Probing the same blots with the human Apo C1 probe demonstrated the human specific 12.3 and 4.8 kb bands associated with the presence of the Kpn I-Cla I fragment derived from the Apo E4 cosmid numbered cosmid 23. The Apo E2 transgenic animal derived from the 267 line, however, lacked both the 12.3 and 4.8 kb fragments. This demonstrated that only the Sca I-Sca I genomic fragment from cosmid 45 (which had the characteristic Apo E 11.1 kb fragment, but lacked the 12.3 and 4.8 kb fragments) was integrated in the 267 line. The Apo E2-222 line, therefore, contained both the Apo E and the Apo C1 gene while the 267 line did not. PCR analysis utilized human specific primers and produced a characteristic 377 bp PCR product specific for the presence of the human transgene in mouse. A routine assay of Apo E4 offspring for the presence of the human Apo E4 gene indicated that animals numbered 42, 43, 44, and 45 possessed the human 377 bp PCR product while Animals 40 and 41 did not inherit the human transgene.

Northern blot analysis of human Apo E transcription:

Total RNA was isolated from mouse brain, liver and kidney using TRIzol reagent (GIBCO-BRL). 50~100 mg of tissues were homogenized in 1 ml of TRIzol reagent and after incubation for 5 minutes at room temperature, 0.2 ml of chloroform was added and mixed well by vigorous shaking. The mixture was separated by centrifugation for 15 minutes at 4° C. and the upper aqueous phase was collected and 0.5 ml of isopropanol was added to precipitate the RNA. The RNA pellet was then washed once with 75% ethanol, lyophilized briefly and resuspended in 50 ul of water. The mRNA was purified from the total RNA using an olig-dT cellulose type 7 column (Pharmacia). The mRNA was fractionated by electrophoresis on a 1.0% formaldehyde-agarose gel and then transferred to GeneScreen membranes. The membrane was probed with Apo E cDNA in 50% formamide/6× SSC at 42° C. and washed at 0.1× SSC at 50° C.

Results:

Northern analysis of RNA isolated from transgenic mouse brain showed the presence of a human Apo E transcript of 1163 bp transcribed in the brain of an Apo E4 transgenic mouse numbered Apo E4–20 but was not present in the brain of a control "knockout" mouse.

Western immunoblot analysis of human Apo E protein:

Mouse proteins were prepared by Dounce homogenization of mouse tissues in TMN buffer (25 mM Tris.HCl [pH 7.6], 3 mM MgCl$_2$, 100 mm NaCl) containing 1 mM phenolmethylsulfonylfluoride (PMSF). 20 ug of the homogenate was mixed with an equal volume of 2× Laemmli loading buffer (100 mm Tris.HCl [pH 6.8], 4% SDS, 10% 2-mercaptoethanol [2-ME], 25% glycerol, and 0.02% bromophenol blue) and heated at 100° C. for 3 minutes. The proteins in the lysate were resolved by electrophoresis in discontinuous polyacrylamide gels (10% polyacrylamide with 3% stacking layer) containing 0.1% SDS (SDS-PAGE). The proteins separated by SDS-PAGE were transferred onto Immobilon membranes (Millipore) using a semi-dry Transblot (Bio-Rad) transfer cell following the manufacturer's protocol. The membrane was blocked in 1.0% bovine serum album (BSA) prepared in 100 mM Tris.HCl pH 7.5, 150 mM NaCl, 0.1% Tween-20 (TBS-T) overnight at 4° C. and then probed with polyvalent goat antiserum against human Apo E (Calbiochem) at 1:5000 dilution for 30 minutes at room temperature. After washing three times with TBS-T, the membrane was exposed to horse antigoat second antibody conjugated with horseradish peroxidase (Calbiochem) at 1:10,000 dilution for 30 minutes at room temperature, and then washed 5–7 times in TBS-T at room temperature. Horseradish peroxidase was visualized with an enhanced chemiluminescence detection kit (Amersham) and exposed to ECL hyperfilm.

Results:

Western blot analysis indicated Apo E4 and Apo E2 transgenic mice expressed the Apo E protein which was not present in the control "knockout" mice.

Measurement of cholesterol:

After an overnight fasting, approximate 250 ul of blood was obtained through tail bleeding or from sacrificed mouse heart. Cholesterol was measured enzymatically using Sigma's Cholesterin detecting kit according to the manufacturer's protocol. The reliability of cholesterol test results was monitored by routine use of control sera with known higher, normal and lower cholesterol concentration (Sigma). 5 ul of mouse serum was mixed with 500 ul of prewarmed cholesterol reagent and incubated at 37° C. for 5 minutes. The cholesterol concentration was calculated by measuring the absorbance at wavelength of 500 nm and using a mathematical formula known in the art.

Results:

Background sera from a mouse tail bleed was assayed for blood cholesterol levels. In the "knockout" mouse, which lacked an Apo E gene to transport cholesterol, blood levels of cholesterol normally averaged five times the level found in normal mice, 400–600 mg/dl versus approximately 100 mg/dl, respectively, on a normal diet of mouse chow. If the human gene had been integrated into the mouse genome and was being expressed, the high cholesterol level of the "knockout" mouse would be corrected or at least substantially reduced due to the ability of the human gene to transport cholesterol in the mouse. The results for the Apo E4 transgene can be seen in Table 1. The human Apo E4 transgenic animals had substantially lower cholesterol levels. The Apo E2 transgenic animal's cholesterol levels were highly variable, however, even between siblings. Since it had been demonstrated that the human gene was present and was being expressed, this variability is believed to reflect how recently the animal had eaten. Homozygous Apo E2 is known to clear cholesterol more slowly than other Apo E isoforms and has been shown, for reasons that are not entirely clear, to be associated with high levels of cholesterol in humans. Thus, the Apo E2 transgenic animals with their highly variable cholesterol levels, in addition to serving as models for the study of the Apo E2 gene in brain, may also be extremely useful for studying the effects of high and low dietary cholesterol levels on lipid transport and metabolism.

TABLE 1

EFFECT OF HUMAN APOLIPOPROTEIN E4 EXPRESSION ON SERUM CHOLESTEROL IN TRANSGENIC MICE.

| Mice | Genotypes | Cholesterol (mg/dl) |
| --- | --- | --- |
| Knockout | K/K | 629.3 ± 70.9 |
| Normal | N/N | 81.6 ± 14.6 |
| Transgenic | E4 (K/K) | 112.0 ± 25.9 |

EXAMPLE 5

Screening Assay

The animals of the present invention are used to screen compounds for the ability to effect the activity of Apo E isoforms. A transgenic mouse produced as described above (e.g., an Apo E4/Apo E4 animal) is administered a test compound (e.g., orally, or by subcutaneous injection) and the effects of the compound on Apo E activity and animal physiology (e.g., life span, brain atrophy, amyloid plaque formation, are compared to such activity and physiology in a control animals (e.g., Apo E2/Apo E2 animals given the same treatment, or the same animals administered a placebo treatment).

The foregoing examples are illustrative of the present invention, and are not to be construed as limiting thereof. The invention is defined by the following claims, with equivalents of the claims to be included therein.

We claim:

1. A transgenic mouse expressing human apolipoprotein E (Apo E) in brain tissue cells, wherein the germ cells and somatic cells of said mouse comprise a transgene encoding said human Apo E in addition to an inactivated endogenous mouse Apo E gene, wherein said transgene includes all regulatory elements of the human Apo E gene necessary for transcription of said transgene in mouse brain, and wherein said human Apo E is expressed in said brain tissue cells throughout the brain development of said mouse at levels sufficient for said mouse to exhibit human Apo E expression patterns found in the human population.

2. A method for screening a compound for the ability to affect the activity of Apo E isoforms and animal physiology in the transgenic mouse of claim 1, comprising:

(a) administering to said transgenic mouse a test compound; and then (b) detecting the effect of the test compound on the activity of Apo E isoforms and the physiology of said mouse, said detectable effect indicating that said test compound affects the activity of Apo E isoforms or animal physiology in said transgenic mouse.

3. A mouse of claim 1, wherein said human Apo E is Apo E4.

4. A mouse of claim 1, wherein said human Apo E is Apo E3.

5. A mouse of claim 1, wherein said human Apo E is Apo E2.

6. A mouse of claim 1, wherein said mouse further expresses said human ApoE in heart, kidney, spleen, muscle, intestine and liver tissue cells.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GGTAGCTAGA TGCCTGGACG G        21

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GCTAGAACCA GCAGAGACCC        20

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GTCTCGGCTC TGAACTACTA TG        22

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GCAAGAGGTG ATGGTACTCG        20